United States Patent
Powell et al.

(10) Patent No.: US 7,914,472 B2
(45) Date of Patent: Mar. 29, 2011

(54) NECK SUPPORT

(76) Inventors: Marcus W. Powell, New London, IA (US); Jesse G. Asper, II, Newburg, PA (US); Tim Keldgord, Jr., Mt. Pleasant, IA (US)

( * ) Notice: Subject to any disclaimer, the term of this patent is extended or adjusted under 35 U.S.C. 154(b) by 0 days.

(21) Appl. No.: 12/030,325

(22) Filed: Feb. 13, 2008

(65) Prior Publication Data

US 2009/0204040 A1 Aug. 13, 2009

(51) Int. Cl.
*A61F 5/00* (2006.01)
*A47B 7/00* (2006.01)
*A47C 20/00* (2006.01)

(52) U.S. Cl. ................... 602/18; 5/622; 5/636

(58) Field of Classification Search .......... 602/17–19, 602/13, 32, 34, 35, 36; 441/118, 119; 5/644, 5/708, 622, 636, 637, 603; 137/859, 517; 2/410, 6.1, 6.2; 128/DIG. 20, DIG. 23
See application file for complete search history.

(56) References Cited

U.S. PATENT DOCUMENTS

| 4,813,899 | A | * | 3/1989 | Fujimoto | 441/122 |
|---|---|---|---|---|---|
| 5,181,279 | A | | 1/1993 | Ross | |
| 5,402,535 | A | | 4/1995 | Green | |
| 5,403,266 | A | * | 4/1995 | Bragg et al. | 602/5 |
| 6,125,478 | A | | 10/2000 | Alaloof | |
| 6,151,735 | A | * | 11/2000 | Koby et al. | 5/644 |
| 6,637,059 | B1 | | 10/2003 | Baker | |
| 7,017,195 | B2 | | 3/2006 | Buckman et al. | |
| 7,089,602 | B2 | | 8/2006 | Talluri | |
| 7,150,048 | B2 | | 12/2006 | Buckman | |
| 2005/0027221 | A1 | * | 2/2005 | Calderon et al. | 602/13 |
| 2006/0217648 | A1 | * | 9/2006 | Rogachevsky | 602/20 |
| 2008/0043076 | A1 | * | 2/2008 | Coffey et al. | 347/92 |

* cited by examiner

*Primary Examiner* — Patricia M Bianco
*Assistant Examiner* — Ophelia Hawthorne

(57) ABSTRACT

A neck support/brace for protecting a neck has a flexible collar with a top wall, bottom wall, sidewalls and sectional walls disposed therebetween that form compartments therein. A plurality of cells are disposed within the compartment. Each of the fluid cells have a valve element disposed therein. When the pressure acting upon the cells is below a threshold pressure, fluid or air flows through the valve element to allow movement of the neck. Alternatively when the pressure on the cells is above the threshold pressure the valve element closes preventing fluid or air flow out of the fluid cell thus causing the cell to stay inflated and provide resistance to a neck movement.

6 Claims, 4 Drawing Sheets

NECK SUPPORT

BACKGROUND OF THE INVENTION

This invention relates a neck support collar. More specifically this invention relates to a neck support collar that allows for neck movement while still protecting the neck under pressure.

Neck supports/braces for athletic and similar activities are well known in the art. Typically, these braces are of a solid construction that, while providing neck support, limit a user's range of motion and are uncomfortable to wear. Other braces, that provide greater comfort, do not provide sufficient support to prevent injuries in the presence of a sudden impact. In addition, current neck braces are not designed to break away in the presence of extreme force. Therefore, a need exists in the art for a neck support that addresses these deficiencies.

An objective of the invention is to provide a neck support that allows for neck movement under normal conditions and support when greater force loads are incurred.

These and other objectives, features, or advantages of the present invention will become apparent from the specification and claims.

SUMMARY OF THE INVENTION

A neck support/brace for protecting a neck has a flexible collar with a top wall, bottom wall, sidewalls and sectional walls disposed therebetween that form compartments therein. A plurality of cells are disposed within the compartment. Each of the fluid cells have a valve element disposed therein. When the pressure acting upon the cells is below a threshold pressure, fluid or air flows through the valve element to allow movement of the neck. Alternatively when the pressure on the cells is above the threshold pressure the valve element closes preventing fluid or air flow out of the fluid cell thus causing the cell to stay inflated and provide resistance to a neck movement.

DETAILED DESCRIPTION OF THE PREFERRED EMBODIMENT OF THE INVENTION

Figure 1:
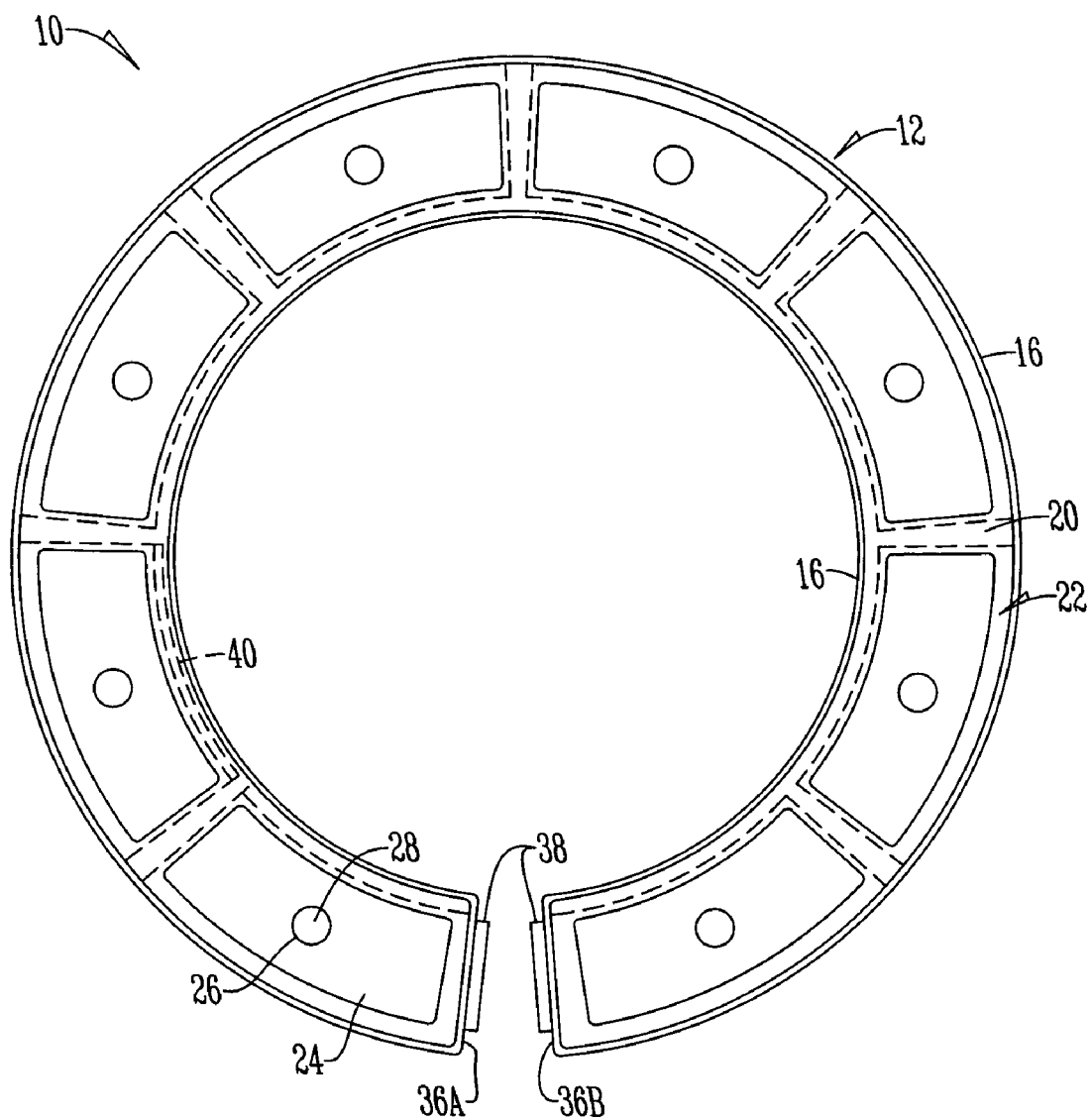
FIG. 1 is a plan view of a neck support.
Figure 2:
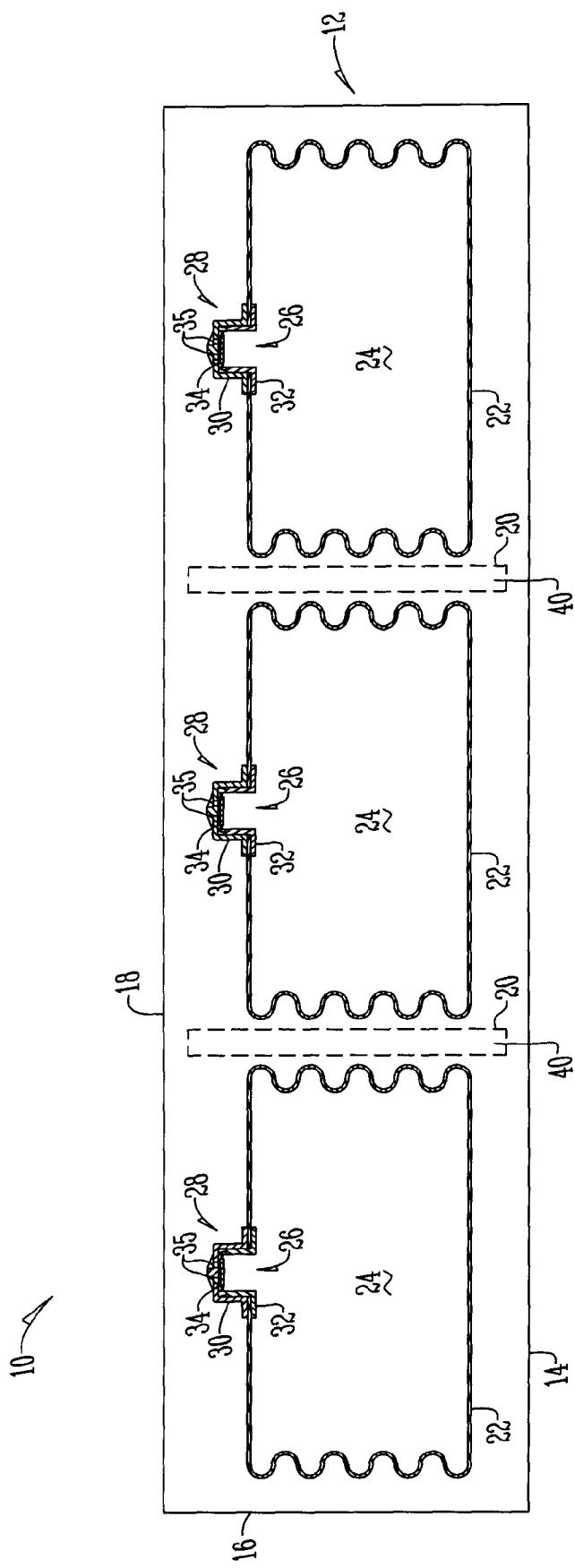
FIG. 2 is a side view of a neck support.
Figure 3:
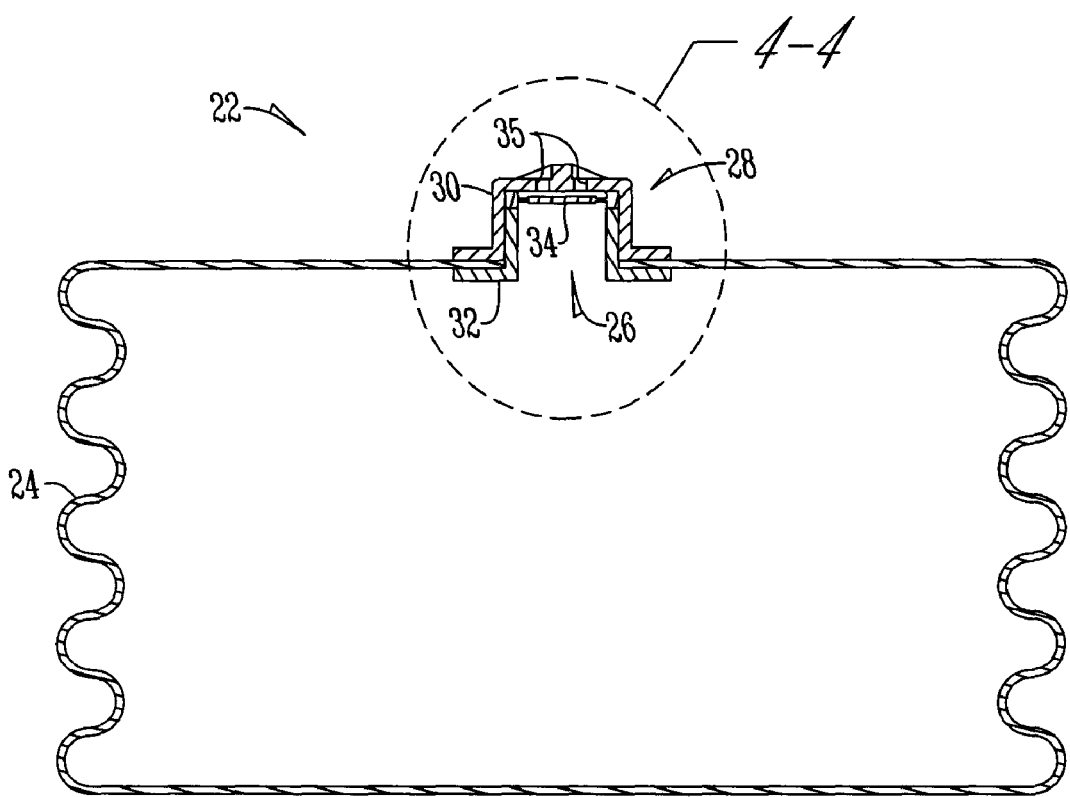
FIG. 3 is a side view of a preferred valve element.
Figure 4:
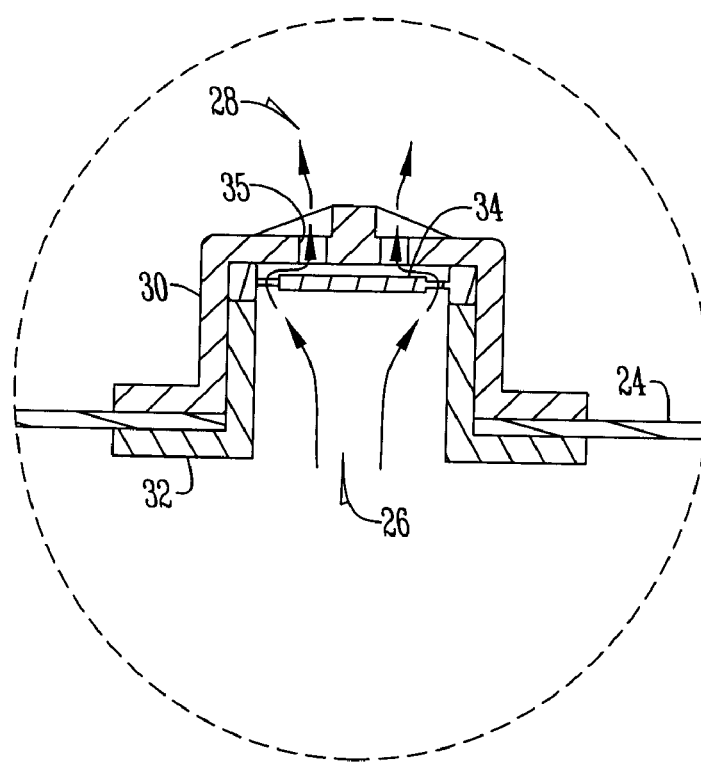
FIG. 4 is a cross-sectional view of a preferred valve element.
Figure 4A:
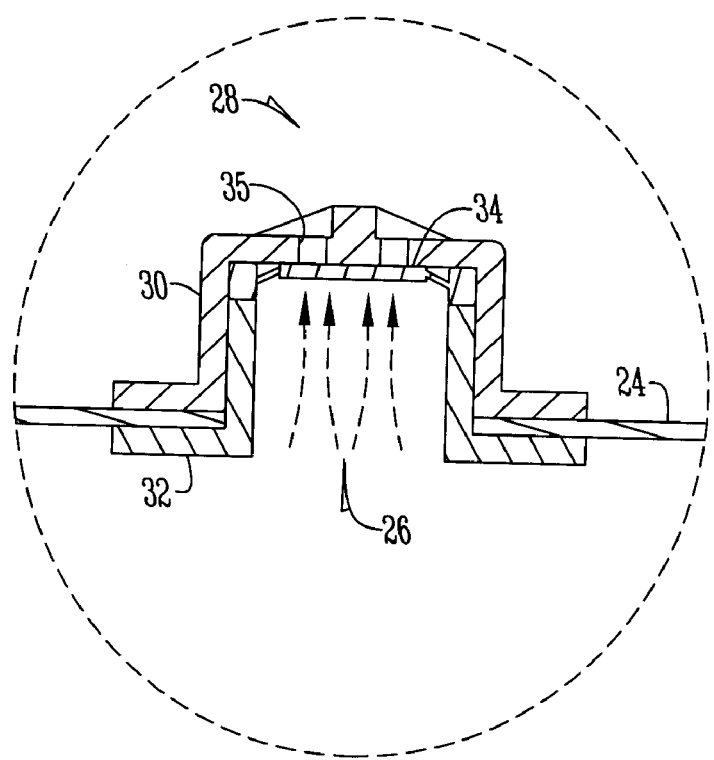
FIG. 4A is a cross-sectional view of a preferred valve element.

Referring to the figures, a neck support is shown by reference numeral 10. While a neck support is shown, by example only, the invention may be adapted for use with a helmet, chest protector, knee support, or the like.

The neck support 10 has a collar 12 having a bottom 14, sidewalls 16, and a removable top wall 18. Sectional walls 20 extend between the sidewalls 16 to form a compartment 22 that snugly receives a cell 24. The cell 24 is made of an elastomer and is of any shape or size. Each cell 24 has a port 26 with a check valve 28 disposed within the port 26.

The check valve 28 is of any type, structure and shape, but preferably has an outer body 30, an inner body 32, and a diaphragm 34 disposed therebetween that is capable of sealing an opening 35 in the inner and outer body. In addition, the check valve 28 preferably permits the release of air from the cell 24 when force is applied below a predetermined threshold level (i.e., under normal movement such as 5 p.s.i.) and prevents the release of air when pressure is applied above a predetermined load (under a high impact load i.e., 15 p.s.i.) based on the support's 10 application.

The ends 36A, 36B of the collar 12 have a connection device 38 that attaches the ends 36A, 36B of the collar 12 to fit about a user's neck. The connection device is of any type such as Velcro®, snaps, ties, buckles or the like and preferably is capable of breaking away in adverse situations such as when the collar 12 catches on an object during an accident.

In one embodiment, the sectional walls 20 have a conduit 40 that provides air ventilation to the interior sidewall 16 of the collar 12. Alternatively the conduits 40 are closed and filled with a cooling gel or fluid.

In operation, the collar 12 is placed around a user's neck and the ends 36A, 36B are connected using the connection device 38. Under normal conditions the user has a full range of neck and head movement. The full range of movement occurs because under small loads (i.e. approximately 5 p.s.i.) the affected cells 24 collapse as air is released through the check valve 28.

Under a higher impact load (i.e., 15 p.s.i.) the brace 10 provides support to the neck because the affected cells do not collapse. The cells do not collapse because the check valves prevent air from escaping from the cell 24 through port 26 at a predetermined level. In the preferred embodiment, under higher impact, air is forced toward port 26 such that the diaphragm moves to seal port 26 and prevent the release of air.

Thus a neck support has been disclosed that, at the very least, meets all of the stated objectives.

It will be appreciated by those skilled in the art that other various modifications could be made to the device without the parting from the spirit and scope of this invention. All such modifications and changes fall within the scope of the claims and are intended to be covered thereby.

What is claimed is:

1. A neck support for protecting a neck comprising:
   a collar having a top wall, a bottom wall, a sidewall, a plurality of sectional walls, and compartments formed between the top wall, side wall, and at least one of a plurality of the sectional walls;
   a plurality of cells disposed within the compartments between the top wall, side wall, and at least one of a plurality of the sectional walls of the collar;
   at least one check valve element disposed within a cell;
   wherein below a threshold pressure air-flows through the check valve element to allow the cell to compress; and
   wherein above the threshold pressure the check valve element prevents air-flow to prevent the cell from compressing.

2. The support of claim 1 wherein the collar has opposite ends that are attached by a connection device.

3. The support of claim 2 wherein the connection device is capable of breaking away in adverse situations.

4. The support of claim 1 wherein the sectional walls have a conduit.

5. The support of claim 1 wherein the check valve element has an outer body, an inner body, and a diaphragm disposed between the inner and outer body.

6. The support of claim 1 wherein the threshold level is 15 p.s.i.

* * * * *